United States Patent [19]

Heinegård et al.

[11] Patent Number: 4,778,768
[45] Date of Patent: Oct. 18, 1988

[54] METHOD OF MONITORING THE PROGRESSIVE DESTRUCTION OF ARTICULAR CARTILAGE IN A JOINT

[75] Inventors: Dick K. Heinegård, Lund; Gert Lindblad, Upsala, both of Sweden

[73] Assignee: Pharmacia AB, Upsala, Sweden

[21] Appl. No.: 732,003

[22] PCT Filed: Jul. 10, 1984

[86] PCT No.: PCT/SE84/00257
§ 371 Date: May 2, 1985
§ 102(e) Date: May 2, 1985

[87] PCT Pub. No.: WO85/01353
PCT Pub. Date: Mar. 28, 1985

[30] Foreign Application Priority Data

Sep. 9, 1983 [SE] Sweden .............................. 8304836

[51] Int. Cl.⁴ ........................................ G01N 33/566
[52] U.S. Cl. ...................................... 436/501; 435/4; 435/7; 436/506; 436/507; 436/509; 436/518; 436/538
[58] Field of Search ............... 435/4, 7; 436/506, 507, 436/509, 518, 512, 538

[56] References Cited

U.S. PATENT DOCUMENTS 4,153,417  5/1979  Hallgren et al. .................... 436/509
4,499,186  2/1985  Tedorescu et al. ................. 436/506

OTHER PUBLICATIONS

Baker, et al., "Methods in Enzymology, vol. 83, (1983), Academic Press, pp. 216–235.

Greiling et al., X1 International Congress of Clinical Chemistry, (1982), Walter de Gruyter, pp. 635–650.

Adam, et al., Articular Synovium Int. Symp., Bruges, (1981), pp. 129–141.

Primary Examiner—Robert J. Warden
Assistant Examiner—Stephen C. Wieder
Attorney, Agent, or Firm—Fred Philpitt

[57] ABSTRACT

Method of determining changes occurring in articular cartilage. The method involves (a) quantifying proteoglycan monomer and/or antigenic fragments thereof in a synovial fluid sample and (b) correlating the values thus obtained with progressive destructions in the articular cartilage appertaining to that sample fluid.

10 Claims, No Drawings

METHOD OF MONITORING THE PROGRESSIVE DESTRUCTION OF ARTICULAR CARTILAGE IN A JOINT

The present invention is concerned with a method of clinically detecting changes occurring in articular cartilage (=the cartilage of skeletal joints). In particular, the invention is concerned with the detection of changes involving progressive destruction of the cartilage, that is, changes indicating a condition of increasing degradation of articular cartilage.

Articular cartilage comprises as its major component an extracellular matrix which assumes an important functional role and the composition of which is controlled by a relatively small number of cells. This matrix is composed of (i) collagen forming a fibrous network which is of importance for the volume stability of the tissue, and (ii), as a further major component, proteoglycan having a large amount of mutually repellant electric charges due to which the tissue acquires its elasticity and its ability to resist compression. Articular cartilage, moreover, contains several other proteins, generally without known functions. An exception to this are the link proteins which participate in the formation of proteoglycan aggregates and contribute to the stability of these aggregates. Such aggregate formation appears to be a prerequisite in order for the proteoglycan and its negatively charged groups to be fixed in the tissue.

Other proteins present in articular cartilage are unknown in respect of their structure and function. Examples of these are two proteins having an apparent molecular weight of about 60 kDa. Moreover, proteins have been detected which are present in most types of cartilage and one of which has a molecular weight of about 36 kDa. Fibronectin, too, can be detected; but its occurrence is actually more conspicuous in other types of connective tissue and in blood plasma.

The structure of cartilage proteoglycans is known nowadays in its major aspects. The molecular unit is the so-called proteoglycan monomer which consists of a central protein core and a large number of carbohydrate side chains carrying a large number of negative charges and attached to the core at one of their ends. The central protein core can be conceived as being subdivided into three regions according to its carbohydrate side chains and its amino acid sequence. The side chains comprise two main types, viz., chondroitin sulfate and keratan sulfate side chains. These two types of side chains are concentrated each to one region of the protein core, to thus form a chondroitin sulfate rich region at one end of the core and a smaller keratan sulfate rich region located between said first-named region and the third core region, this latter being the hyaluronic acid-binding region which does not possess any carbohydrate side chains of the aforesaid types. The predominant proteoglycans contain about 100 chondroitin sulfate chains each with 100 negative charges, and about 50 keratan sulfate chains each with about 5 negative charges, the total of charged groups being about 10,000. Via the hyaluronic acid-binding region a great number of proteoglycan monomers are bound to hyaluronic acid which consists of a long polysaccharide chain. The aggregates thus formed have molecular weights exceeding $100 \times 10^6$ Da. The overall compositional pattern is further complicated by the fact that articular cartilage contains two antigenically different populations of aggregating proteoglycans differing slightly inter se in respect of the nature of their side chains. By means of an immunochemical method small amounts of proteoglycans have been characterized in biopsies from cartilage (Biochem. J. (1979), p. 35–45, and Biochem. J. 187 (180), p. 687–694).

Degradation of cartilage structures is believed to involve the whole extracellular matrix, although different parts are degraded in different stages of a cartilage disease. In an early phase, mainly proteolycans are degraded, while the collagen remains in the matrix. Unpublished results indicate that in the very beginning only the two carbohydrate rich regions are degraded and excreted to the synovial fluid, while the hyaluronic acid binding region remains bound to the extracellular matrix for a longer time.

Prior to the invention no methods were available to detect changes at this early stage and only later in the destructive process arthroscopy could be used as a diagnostic tool. The macroscopic, probably irreversible changes appear as a consequence of further degradation involving both proteoglycan and collagen. At the later stages nearly all the proteoglycan will be lost meaning that the cartilage will become rather static with respect to its proteoglycan content.

Degradation of structures in articular cartilage is seen typically in all diseases resulting chronically in the destruction of the joint structures. As examples of such disorders may be mentioned rheumatoid arthritis, psoriasis arthritis, and osteoarthrosis. Acute inflammation of a joint, too, is often accompanied by a destruction of cartilage, although in most cases this will not develop into the chronically destructive disease. It is not known which factors are crucial for the acutely inflamed joint to either proceed to healing or develop into the chronic process. Examples of diseases involving acute joint inflammation are yersinia arthritis, pyrophosphate arthritis, gout (Arthritis urica), septic arthritis and various arthrites of traumatic etiology. Among other factors potentially conducive to the destruction of articular cartilage may be mentioned, for instance, treatment with cortisone; this has been known for a long time to accelerate the degenerative process in osteoarthrosis. It should be noted, however, that the actual conditions prevailing in cases of arthritis with severe inflammation of the joint are of a rather more complex character, since in those cases injection of cortisone appears to have an overall positive effect. An object of the present invention is to improve the diagnostic possibilities of cartilage degenerative processes, particularly in early stages, and to provide a means of checking up on or monitoring the effects of therapeutical measures taken.

Heretofore diseases of the joints have mostly been diagnosed by indirect methods. For example, inflammatory processes have been detected by demonstration of increased amounts of leucocytes in samples of synovial fluid. In addition, the function of the joint has been determined, and also the sensation of pain from the joint has been studied. As regards cartilage biopsies, these have been available only in a very late stage, usually in connection with actual surgery; only in that late stage has it been possible, thus, to study changes in the composition of the cartilage. The problem inherent in this type of biopsy is (i) that it has to be taken from the very portion of the cartilage in which the changes have occurred, and (ii) that such biopsies are often taken in so late a stage that most of the primary changes have already subsided.

A rudiment of an alternative method was published in 1967 by Sandson (Science 155 (1967), p. 839–841). Sandson described a "new component". This was detected by cross reaction with an antibody preparation prduced by immunization of rabbits with a partially purified cartilage extract. Preparations of the type employed have later been shown to contain a large number of different proteins. Results obtained with these preparations would generally tend to vary, and for this reason it has now for a long time been customary to adopt a different technique in the cartilage field; in view of this circumstance it is not possible now to give any definition of the contents of these preparations. Sandson found that the "new component" was likely to be present in increased amounts in certain disease conditions. At the same time he showed, together with Janis R. et.al. (Science 158 (1967), p. 1464–67), that the lining cells of the synovial membrane contained a component antigenically related to the aforesaid "new component". Sandson and Janis suggested that this component might pass into the synovial cavity from the synovial membrane. These lining cells are not known to contain proteoglycan of the kind that is typical of articular cartilage, and as a consequence the Sandscn method has not provided a means of measuring specifically proteoglycan monomers deriving from articular cartilage.

A similar methodology has recently been applied by Gysen P. et al. (Articular Synovium Int. Symp. (1982) p. 129–41) who used a competitive solid phase immunoassay (labelled proteoglycan and a solid phase antiproteoglycan antiserum) in order to determine the proteoglycan content of synovial fluids from patients suffering from rheumatoid arthritis and osteoarthrosis. In their study they only found very low values which were related to an enhanced phagocytosis by certain cells not being part of the articular cartilage. On the basis of research results obtained in connection with the present invention, these low values must be interpreted as if the studied cartilage was in a very late phase of destruction. Both Gysen, P. et al. and Sandson thus only examined very late stages of cartilage destruction.

It will thus be appreciated that numerous disadvantages have been involved with earlier methods for specifically measuring changes occurring in an articular cartilage. In many respects these disadvantages are eliminated by the present invention. The method of this invention for determining changes occurring in articular cartilage is characterized in that the concentration or quantity of cartilage proteoglycan monomer or antigenic fragments thereof is determined specifically in a synovial fluid sample from the synovial cavity bordering on the articular cartilage in question, and that the value obtained is compared with a reference value from an earlier analysis. The term "proteoglycan" will hereinafter be used synonymously for the aforesaid fragments and for the monomer. In the light of what is known to date, an increased concentration or quantity (level) means that the cartilage is subject to progressive destruction. The said increase is measured in relation to the reference value obtained for the/a joint having healthy cartilage. A decreased concentration relatively to that same reference value may indicate that proteoglycans have an impaired ability to migrate into the synovial fluid. During the priority year research work has shown that a decreased amount (relatively that same value for a healthy joint) may point to the fact that the total amount of proteoglycans in the cartilage is substantially decreased, indicating tissue loss. As a consequence only a lower amount of proteoglycans remains to be subjected to the destructive process meaning that, with regard to proteoglycan, the destruction is at or close to its endpoint.

Thus in acccrdance with the present invention in its general aspect specific proteoglycans from articular cartilage are quantified in a sample of synovial fluid by means of known per se methods, whereupon the value thus obtained is compared with a reference value from an earlier analysis, either on the same point or as a mean value obtained for healthy joints, a difference between these values reflecting a change that has taken place in the articular cartilage corresponding to said sample. Various embodiments of the invention are set forth in the appended claims.

In its preferred embodiments the invention is characterized in that the determining of the content of proteoglycan monomer or its antigenic fragment is carried out with the aid of an immunochemical assay method. According to these embodiments of the invention, at least one antibody preparation (henceforth to be called antiproteoglycan) having specificity for antigenic determinants on the proteoglycan is added to the sample in order to thus react with proteoglycan present in the sample, the amount of proteoglycan in the sample being then determined in a known per se manner. The antiproteoglycan employed may be directed specifically against structures in one, two or three regions of the three-pestide regions of the proteoglycan monomer. One of the preferred embodiments of the invention comprises determining the concentration or amount of the region(s) corresponding to the specificity of the antiproteoglycan employed. As already indicated, when very early stages of destructions are to be determined, it is most preferable to use an antiproteoglycan specific for one or more determinants present in any of the two carbohydrate rich regions of the proteoglycan core.

It will be seen from the above explanations that for determining the proteoglycan monomer or fragment content the invention in its preferred embodiments utilizes an antigenantibody reaction, thus these modes encompass a method selected from the large group of immunological assays. A multitude of different methods belonging to this group are known to persons skilled in the art. All of these methods are potentially applicable to the invention, although some of them are more eminently suitable than others, for example because of the specificity inherent in a special technique, or because of a high degree of sensitivity or selectivity. Methods to be mentioned in this context are e.g. those employing a labeled reactant, for instance an antigen or antibody labeled with an analytically traceable label group; examples of such labels are a radioactive isotope, an enzyme, an enzyme substrate, an enzyme inhibitor, a fluorescent or chemoluminescent group, a particle, a bacteriophage or other known labels. In the context of the present invention either the proteoglycan or the antiproteoglycan or an antibody preparation reacting with an antiproteoglycan may preferably be labeled and used according to the invention When measuring fragmented proteoglycans by the use of labeled proteoglycan, it is imperative to use either labeled forms of the fragments to be, determined or to use antibody only reacting with antigenic sites, common for such fragments and labeled molecules.

In immunological assay methods of the type as mentioned above, the labeled reactant such as for instance a labeled antigen is caused to react with its immunochemical counterpart, for instance its antibody. If labeled antigen and antibody are used, the reaction between them will give a labeled antigen-antibody complex, with or without residual free labeled antigen and free antibody remaining in the reaction mixture. In this context "free" means that the antigen or antibody, resp., does not form part of the complex. After the reaction, the analytically traceable group is determined in free labeled antigen or in the complex. The labeled reactant and its amount have been chosen so that the value measured is a function of that to be determined.

For the discrimination between free labeled reactant and complex-bound labeled reactant two main types of practical methods are available, viz., homogeneous and heterogeneous methods.

Homogeneous methods utilize the phenomenon that the activity of a label group will vary depending on whether or not said group is bound in a complex. It is thus possible to assay for complex-bound and/or free labeled reactants without proceeding to their physical separation from each other.

Heterogeneous methods involve separation of complex-bound labeled reactant from free labeled reactant. This separation may be accomplished in exxentially two different ways: (1) One separation method utilizes a soluble or insoluble reagent which selectively precipitates or adsorbs (a) the complex (containing labeled reactant) but not free labeled reactant, or (b) free labeled reactant but not complex-bound labeled reactant. The terms "selective precipitation" and "selective adsorption" mean that one species is precipitated or adsorbed to a greater extent than the other. Examples of precipitating reagents are polyethylene glycol and precipitating antiserum directed against some complex component that is not labeled. (2) The other method utilizes an insoluble or insolubilizable support to which is bound a non-labeled antigen, non-labeled antibody or non-labeled anti-antibody. Just as in method (1) two phases are formed, one of these phases being enriched in free labeled reactant and the other one being enriched in complex-bound labeled reactant. The two phases are then separated from each other, whereupon the analytically traceable group is determined in at least one of the phases.

The supports employed and their use belong to prior art technique. Suffice it to mention here that hydrophobic plastics surfaces may be employed such as for instance surfaces of polyvinyl chloride or polystyrene to which an immunochemical reactant can be adsorbed or bound. Other types of supports are insoluble supports containing hydroxyl, amino, carboxyl or amide groups; to these the immunochemical reactants may be bound covalently. In some cases it is advantageous to adsorb the immunochemical reactant to the support.

According to still another way of subdividing or grouping immunological assay methods employing labeled reactants, one such group comprises competitive methods and the other group comprises non-competitive methods. The term "competitive" refers to the phenomenon that a pair of different immunochemical reactants are able to compete for a site on an immunochemical counterpart that is common to both. Examples of such reactants are labeled and non-labeled antigen. A competitive method with them will thus involve inhibition of a reaction between labeled antigen and the corresponding antibody by non-labeled antigen. Still another example of this type of reactants are soluble and insolubilized antigen. Among immunological methods that do not utilize labeled reactants may be mentioned various electrochemical, immunodiffusion and electrophoresis methods. Particularly worth mentioning among these latter methods are Laurell's rocket method (Laurell C-B, Anal. Biochem. 15 (1966), p. 45- ) and Mancini's diffusion method (Mancini G. et.al., Immunochemistry 2 (1965), p. 235- ). Other examples are the so-called agglutination methods.

In these assay methods it is in some cases possible to equivalently make use of biospecific affinities other than the antigen-antibody affinity. Examples of pairs of compounds having such other-type affinity to each other are protein A -IgG, carbohydrate - lectin, Clq - immunocomplex, RF factor -immunocomplex, biotin - avidin, etc.

In the hitherto best known and most advantageous embodiment of the invention, a labeled reactant and a competitive heterogeneous system are employed. In this embodiment of the invention a proteoglycan bound to a support is allowed to compete with the proteoglycan of the sample in respect of the added amount of antiproteoglycan. The antiproteoglycan will bind to the support in an amount inversely proportional to the proteoglycan content in the sample. The thus resultant support-bound antiproteoglycan is detected and quantified with an anti-antibody directed against the antiproteoglycan and labeled with an analytically traceable group. For best results it is suitable to preincubate the sample with antiproteoglycan before the support-bound antigen (support-bound proteoglycan) is added.

Proteoglycan corresponding to separated monomeric subpopulations and their different peptide regions is produced in a manner known per se, utilizing for example density gradient centrifugation in CsCl, zonal rate centrifugation, fragmentation with proteolytic enzymes followed by centrifugation and/or gel chromatography. In the embodiment of the invention employing the immunochemical assay route it is recommendable before carrying out the assay to depolymerize the chondroitin sulfate side chains of the proteoglycan, e.g. by means of chondroitinase digestion to thus unmask antibody-binding sites. This applies both to the sample and to the proteoglycan participating in the antigen-antibody reaction of the assay.

As regards the production of antiserum and antibodies specifically directed against one of the peptide regions of the monomer, this too is a known per se method. However, it has been found that for certain modes of the invention it may be advantageous to immunize with intact proteoglycan monomers. An antiserum thus produced may contain antibodies specific for the different determinants of the proteoglycan; it may thus be employed as a universal reagent in the method according to the present invention. Very probably the use of preparations of so-called monoclonal antibodies or polyclonal antibodies raised against substructures of the proteoglycan and directed against different determinants on the proteoglycan will be conducive to advantageous embodiments. Among the different regions of the proteoglycan core, the hyaluronic acid binding region has the highest immunogenicity. This means that in order to obtain a good antibody preparation for the measurement of proteoglycan fragments deriving from the other two regions, an antigenic preparation only containing determinants from these two regions should be used for immunizing purposes.

The synovial fluid sample is obtained in a manner known per se, for instance by suction from the synovial cavity. Synovial fluid is a highly viscous liquid which is very difficult to handle. It is therefore recommendable to decrease the viscosity of the sample, for instance by treatment with chondroitinase; but an important point to be observed is that the decrease in viscosity must not have any adverse effect on the quantification procedure. Thus if an immunochemical method is employed for the quantification it is imperative that the antibody-binding sites on the proteoglycan are not destroyed.

The invention is further illustrated in the below working examples.

EXAMPLE 1

Determining changes in animal articular cartilage

A. Preparing antigens

Proteoglycans were extracted from bovine nasal cartilage or canine hip articular cartilage. The extracts were purified by means of CsCl density gradient centrifugation under dissociative conditions in guanidinium chloride (4M aqueous solution). Subpopulations of proteoglycans rich in chondroitin sulfate (referred to as D1-S1) and proteoglycans rich in keratan sulfate (D1-S2) were prepared separately. The aforesaid preparations were made in conformity with the teachings of Heinegård, D. et.al. (Seminars Arthr. Rheum. 11:1 (1981) (Suppl. 1) p. 31–33). Proteoglycan preparations employed for immunization were made in the same manner as above and subjected to final purification by means of gel chromatography on Sephadex® G-200 (dextran cross-linked with epichlorohydrin, Pharmacia Fine Chemicals AB, Uppsala, Sweden) which was eluted with 4M guanidinium chloride (Wieslander J. et.al., Biochemical Journal 179 (1979) p. 35–45). Before a preparation was employed as an antigen in an assay in accordance with the present invention the chondroitin sulfate chains in the proteoglycans were removed by digestion with chondroitinase ABC (Miles Chemicals, USA). For this purpose, the preparations were dissolved in 0.05M Tris-HCl, pH 7.5, to a concentration of 1 mg/ml, and were digested for 6 hrs at 37° C. Dilutions of the digested samples were employed without further treatment.

B. Synovial Fluid

Samples of synovial fluid were taken from the left knee joint of each of nine dogs which had been subjected to surgery in the left knee joint so as to develop osteoarthrosis therein. Similar samples were taken from the right knee joint as controls. The samples from both knee joints were taken on the day of surgery, whereupon the posterior cruciate ligament of the left joint was cut off in accordance with Nuki (as a reference see McDevitt et.al., J. Bone Joint Surg. Br. Vol. 58-B (1976) p. 94–101). After 3, 6, 10, 15, 19, 26 and 29 weeks samples were taken by aspiration of available synovial fluid from both the left joint which had been operated on and the right joint which was to serve as control. In several instances sampling attempts were unsuccessful which is indicated by gaps in Tables 1 and 2. The reason why these attempts failed is that the volumes of synovial fluid available were very small, especially in the control joints. Prior to being analyzed the samples were digested with chondroitinase for the purposes of depolymerizing hyaluronate and removing the chondroitin sulfate side chains, all this in accordance with one of the preferred embodiments of the invention. The digestion procedure comprised, as a first step, a partial digestion for reducing the viscosity of the synovial fluid to thus facilitate handling of the sample. This was accomplished by adding 2 μl (1% of the sample volume) of an aqueous solution containing 0.01 (nominal) units of chondroitinase ABC in 1.25M Tris-HCl, pH 8.0. After 4 hrs at 37° C., 50 μl samples were taken from the digest and were mixed with 400 μl of an aqueous solution containing 0.1M Tris-HCl, pH 8.0, and 0.01 units of chondroitinase ABC. After incubation at 37° C. for another 4 hrs digestion of the chondroitin sulfate chains was complete, and the samples were then frozen at −30° C. to be kept in that state until they were to be used.

C. Preparing Antisera

Antibodies were raised in rabbits immunized with protecglycan from canine hip articular cartilage (The proteoglycan was obtained analogously to the procedure in A omitting the chondroitinase digestion). An initial injection of 1.5 mg proteoglycan monomer in Freund's complete adjuvant was followed by two monthly injections of 1.0 mg proteoglycan monomer in Freund's incomplete adjuvant. Thereafter the antibody titer was sufficient for being used in an immunoassay. The serum was not purified before being employed in accordance with the invention.

D. Enzyme Immunosorbent Method (ELISA)

Microtiter plates employed were polyvinyl chloride plates (Dynatech (M 29), Alexandria, Va, USA). The wells were coated (24 hrs, room temperature) with 200 μl of a proteoglycan preparation corresponding to chondroitinsulfate-rich proteoglycans (2 μg/ml; D1-S1) or to keratansulfate-rich proteoglycans (0.5 μg/ml; D1-S2), both produced in accordance with paragraph A above, optionally with omission of the chondroitinase treatment mentioned in said paragraph.

Stock solutions (0.5 mg/ml in 0.05 Tris-HCl, pH 8.0) of these proteoglycan preparations were digested with chondroitinase ABC, (0.01 units/mg) for 4 hrs at 37° C. before being further diluted (0.05M Tris-HCl, pH 8.0) and employed for coating the wells. The coated microtiter plates were carefully rinsed with an aqueous solution containing 0.15M sodium chloride, 0.05 % Tween® 20 (polyoxyethylene sorbitan monolaurate) in order to remove non-specific non-bound proteoglycan. Synovial fluid samples (50 μl) digested with chondroitinase in accordance with B above were diluted with 750 μl of an aqueous solution containing 0.10M sodium chloride, 0.05M sodium phosphate, 0.05 % (w/v) Tween® 20, pH 7.5. Samples (110 μl) of the dilutions were mixed with an equal volume of a dilution in the same buffer of rabbitanti(proteoglycan) specific for the proteoglycan monomer and obtained in accordance with paragraph C above. After preincubation for 24 hrs at room temperature 200 μl of the mixture (in triplicate) were added to the wells of the microtiter plate. After a 60 min. incubation period at room temperature the plates were rinsed as stated above. Next followed an addition of 200 μl of a 1/150 dilution of swine-antirabbit IgG conjugated with alkaline phosphatase (Orion Diagnostica, Helsinki, Finland) in an aqueous solution containing 0.10M sodium chloride, 0.05M sodium phosphate, 0.05% Tween® 20, 2 mg/ml bovine serum albumin, pH 7.5. After a further 60 minutes at room temperature the wells were rinsed again, and this was then followed by addition of 200 μl of an enzyme substrate solution containing 1 mg/ml p-nitrophenyl phosphate, 1M diethanolamine, 0.5M MgCl$_2$ and having a pH of 9.8. Absorbance at 405 nm was measured at the start and after a 60 min. period of incubation at room temperature. The increase in absorbance served as a basis for the calculations. A standard curve was obtained by means of performing the procedure also with samples containing known amounts of canine proteoglycan monomer (digested with chondroitinase ABC). These standard samples were included in each microtiter plate. All samples were analyzed in triplicate, the mean value then being employed for calculations carried out with the aid of a spline function. The results are set forth in Tables 1 and 2.

EXAMPLE 2

Tests were made analogous to Example 1, with the only difference that polystyrene cuvettes were coated instead of microtiter plates. The cuvettes were employed as the solid phase in accordance with the invention. The results were showed a somewhat large coefficient of variation than those obtained in Example 1.

EXAMPLE 3

Tests were run in the same manner as in Example 1 except that combinations of homologous antigens were employed, that is, canine proteoglycan for coating, samples from dogs, and canine proteoglycan for immunization. The results obtained were similar to those of Example 1.

EXAMPLE 4

Determining Changss in Human Articular Cartilage

Synovial fluids from a number of patients were analyzed in a manner analogous to that described in Example 1. The diagnoses recorded were confirmed by arthroscopy and/or clinically. The results are set forth in Table 3. They demonstrate highly increased values for disease conditions involving destruction of joints.

EXAMPLE 5

Detection of Changes During Treatment with Cortisone

Cortisone (Celestona ® biphase, Schering AG, Berlin, Federal Republic of Germany; and Depomedron ®, The Upjohn Company, Kalamazoo, Mich., U.S.A.) were injected in normal vertebral joints of horses. In the case of Celestona ® biphase injections the dose was 4 ml/injection (6 mg/ml), whereas in the case of Depomedron ® injections the dose has 2 ml/injection (4 mg/ml). Every other joint was injected with cortisone and every other with only physiological saline. Injections were administered once a week for 3 weeks, and at the same time synovial fluid samples were taken. The content of proteoglycan antigen was determined in the manner as indicated in Example 1D, but the antigen employed was proteoglycan monomer isolated from equine articular cartilage. The antiproteoglycans employed were directed against a mixture of aggregating proteoglycans derived from bovine nasal cartilage and prepared in a manner similar to that of Example 1A. The values obtained are set forth in Table 4. They show that cortisone injections in healthy joints result in a substantially increased release of proteoglycan into the synovial fluid, thus revealing that the articular cartilage is being progressively destroyed. In a similar manner it is possible to monitor treatments given for the prevention of proteoglycan degradation in articular cartilage.

TABLE 1

Concentration of proteoglycan fragments in synovial fluid samples.
Wells coated with proteoglycan rich in chondritin sulfate (D1-S1)
Values expressed as μg/ml of proteoglycan equivalents.

| SYNOVIAL FLUID Number of after-surgey weeks when samples were taken | DOG NO. | | | | | | | | | | | | | | | | Difference between this sample and that taken before surgery |
|---|---|---|---|---|---|---|---|---|---|---|---|---|---|---|---|---|---|
| | I | | II | | III | | IV | | V | | VI | | VII | | VIII | | IX | |
| | l | r | l | r | l | r | l | r | l | r | l | r | l | r | l | r | l | r | |
| Before surgery | 77 | — | 37 | — | 71 | — | 72 | — | — | — | — | — | — | — | — | — | — | — | p = 0.1 |
| 3 | 252 | 107 | 83 | 81 | — | — | 177 | — | 105 | 26 | 73 | — | — | — | 90 | — | 23 | — | p < 0.025 |
| 6 | 197 | — | 95 | 73 | 134 | 123 | 123 | — | 113 | 82 | 105 | — | 71 | 37 | 84 | — | 50 | 24 | p < 0.15 |
| 10 | 152 | 73 | 87 | — | 89 | 104 | 67 | — | — | — | 76 | 32 | 65 | 19 | — | — | 48 | 35 | p < 0.05 |
| 15 | 179 | 30 | 74 | 88 | 230 | — | 128 | — | 205 | — | 83 | — | 52 | 32 | — | — | 31 | 29 | p < 0.025 |
| 19 | 135 | 90 | 94 | 111 | 149 | — | 198 | — | 70 | — | 94 | — | 69 | 61 | 118 | 73 | 39 | — | p < 0.15 |
| 26 | 86 | 44 | 73 | — | — | — | 88 | — | 115 | — | 48 | 29 | 60 | — | 53 | — | 26 | 33 | p > 0.2 |
| 29 | — | 291 | 145 | — | 63 | 41 | 121 | — | 75 | 23 | 28 | 19 | 79 | — | — | — | 35 | | | p = levels of significance
l = left
r = right

TABLE 2

Concentration of proteoglycan fragments in synovial fluid samples.
Wells coated with proteoglycan rich in keratan sulfate (D1-S1).
Values expressed as μg/ml of proteoglycan equivalents.

| SYNOVIAL FLUID Number of after-surgey weeks when samples were taken | DOG NO. | | | | | | | | | | | | | | | | Difference between this sample and that taken before surgery |
|---|---|---|---|---|---|---|---|---|---|---|---|---|---|---|---|---|---|
| | I | | II | | III | | IV | | V | | VI | | VII | | VIII | | IX | |
| | l | r | l | r | l | r | l | r | l | r | l | r | l | r | l | r | l | r | |
| Before surgery | 49 | — | 53 | — | 55 | — | 56 | — | — | — | — | — | — | — | — | — | — | — | |
| 3 | 137 | 41 | 74 | 84 | — | — | 168 | — | 104 | 40 | 29 | — | — | — | 60 | — | 43 | — | p < 0.15 |
| 6 | 54 | — | 134 | 49 | 86 | 70 | 148 | — | 88 | 103 | 58 | — | 79 | 43 | 119 | — | 68 | 23 | p < 0.1 |

TABLE 2-continued

Concentration of proteoglycan fragments in synovial fluid samples.
Wells coated with proteoglycan rich in keratan sulfate (D1–S1).
Values expressed as µg/ml of proteoglycan equivalents.

| SYNOVIAL FLUID Number of after-surgery weeks when samples were taken | DOG NO. I | | II | | III | | IV | | V | | VI | | VII | | VIII | | IX | | Difference between this sample and that taken before surgery |
|---|---|---|---|---|---|---|---|---|---|---|---|---|---|---|---|---|---|---|---|
| | l | r | l | r | l | r | l | r | l | r | l | r | l | r | l | r | l | r | |
| 10 | 66 | 58 | 81 | — | 68 | 61 | 53 | — | — | — | 45 | 31 | 58 | 32 | — | — | 37 | 42 | $p < 0.15$ |
| 15 | 61 | 27 | 69 | 101 | 127 | — | 89 | — | 166 | — | 53 | — | 58 | 43 | — | — | 53 | 31 | $p < 0.1$ |
| 19 | 53 | — | 94 | 81 | 75 | — | 94 | — | 95 | — | 52 | — | 57 | 92 | 94 | 184 | 38 | — | $p < 0.1$ |
| 26 | 42 | 34 | 45 | — | — | — | 80 | — | 93 | — | 25 | 24 | 50 | — | 42 | — | 30 | 30 | $p > 0.2$ |
| 29 | — | 95 | 117 | — | 40 | 38 | 92 | — | 103 | 38 | 27 | 27 | 114 | — | — | — | 37 | — | $p < 0.2$ | p = levels of significance
l = left
r = right

TABLE 3

| Diagnosis of patients | Proteoglycan µl/ml |
|---|---|
| Swollen joint, normal cartilage | 41 |
| Swollen joint, no changes in cartilage | 35 |
| Normal | 33 |
| Rupture of meniscus, throughout with lesion of substance | 81 |
| Yersinia arthritis | 353 |
| Pyrophosphate arthritis, synovitis | 172 |
| Rheumatoid arthritis | 100 |
| Visible cartilage destruction ("torn cartilage, with lesions of femoral condyles); gout | 81 |

TABLE 4

| | Proteoglycan concentration µg/ml | | | |
|---|---|---|---|---|
| Week No. | Cortisone inj | Placebo | Cortisone inj | Placebo |
| Inj 1 | 0 | 103 | 120 | 99 | 105 |
| Inj 2 | 1 | 2 795 | 104 | 1 515 | 76 |
| Inj 3 | 2 | 2 660 | 116 | 3 137 | 58 |
| | 3 | 2 829 | 218 | 3 626 | 72 |
| | 4 | 465 | 58 | 189 | 57 |
| | 5 | 130 | 70 | 768 | 38 |
| | 6 | 41 | 54 | 72 | 46 |
| Inj 1 | 0 | 49 | 37 | 57 | 69 |
| Inj 2 | 1 | 1 161 | 47 | 581 | 65 |
| Inj 3 | 2 | 1 466 | 44 | 1 640 | 69 |
| | 3 | 1 259 | 43 | 941 | 57 |
| | 4 | 54 | 32 | 83 | 47 |
| | 5 | 38 | 25 | 48 | 43 |
| | 6 | 29 | 23 | 38 | 37 |

We claim:

1. An immunological method for monitoring the progressive early phase destruction of articular cartilage in a joint which comprises the steps of
   (a) obtaining a first synovial fluid sample from a joint,
   (b) on at least one later occasion obtaining a least one other synovial fluid sample from said joint,
   (c) reacting said fluid samples with an antibody specific to proteoglycan monomers recognized to contain three peptide regions or specific to antigenic fragments thereof existing in the synovial fluid samples withdrawn in accordance with steps (a) and (b),
   (d) quantifying said monomers or fragments thereof, and
   (e) comparing the quantities found in accordance with step (d),
whereby the degree of progressive early phase destruction of the articular cartilage in said joint at said later occasion may be ascertained by observing the magnitude of the increased proteoglycan values relative to the proteolgycan value found for said first fluid sample.

2. A method according to claim 1 wherein the immunological assay is performed with an antibody preparation directed specifically against at least one of the three peptide regions of the proteoglycan monomer.

3. A method according to claim 2 wherein antibody-binding sites in said proteoglycan monomer or in said antigenic fragments thereof have been unmasked by depolymerizing the chondroitin sulfate side chains of the proteoglycan in order to facilitate a proteoglycan-antiproteoglycan reaction.

4. A method according to claim 2 wherein the immunological assay method is a heterogenuous method.

5. A method according to claim 4 wherein proteoglycan monomer or antigenic fragments thereof are bound to an insoluble support and are allowed to compete with the sample proteoglycan for antiproteoglycan, whereupon the antiproteoglycan thus insolubilized is quantified with the aid of labeled antibodies directed against the antiproteoglycan.

6. An immunological method for estimating the progressive early phase destruction of the articular cartilage in a joint which comprises the steps of
   (a) obtaining a synovial fluid sample from a first healthy joint,
   (b) obtaining at least one synovial fluid sample from a second joint,
   (c) reacting said fluid samples with an antibody specific to proteoglycan monomers recognized to contain three peptide regions or specific to antigenic fragments thereof existing in the synovial fluid samples withdrawn in accordance with steps (a) and (b),
   (d) quantifying said monomers or fragments thereof, and
   (e) comparing the quantities found in accordance with step (d),
whereby progressive early phase destruction of the articular cartilage in said second joint is indicated by a proteoglycan value in the sample of step (b) that is higher than the proteoglycan value obtained from the sample from said healthy joint.

7. A method according to claim 6 wherein the immunological assay is performed with an antibody preparation directed specifically against at least one of the three peptide regions of the proteoglycan monomer.

8. A method according to claim 6 wherein antibody-binding sites in said proteoglycan monomer or in said antigenic fragments thereof have been unmasked by depolymerizing the chondroitin sulfate side chains of the proteoglycan in order to facilitate a proteoglycan-antiproteoglycan reaction.

9. A method according to claim 6 wherein the immunological assay method is a heterogenous method.

10. A method according to claim 9 wherein proteoglycan monomer or antigenic fragments thereof are bound to an insoluble support and are allowed to compete with the sample proteoglycan for antiproteoglycan, whereupon the antiproteoglycan thus insolubilized is quantified with the aid of labled antibodies directed against the antiproteoglycan.

* * * * *